United States Patent [19]

Angelsen et al.

[11] Patent Number: 4,559,952
[45] Date of Patent: Dec. 24, 1985

[54] METHOD OF ULTRASONICALLY MEASURING BLOOD FLOW VELOCITY

[75] Inventors: Bjorn A. J. Angelsen; Kjell Kristoffersen, both of Trondheim, Norway

[73] Assignee: Vingmed A/S Inkognitogt, Oslo, Norway

[21] Appl. No.: 440,255

[22] Filed: Nov. 9, 1982

[30] Foreign Application Priority Data

Nov. 13, 1981 [NO] Norway ................................. 813848
Apr. 16, 1982 [NO] Norway ................................. 821245

[51] Int. Cl.$^4$ ............................................. A61B 10/00
[52] U.S. Cl. ..................................................... 128/663
[58] Field of Search ................................ 128/660–661, 128/663; 73/826, 861.25

[56] References Cited

U.S. PATENT DOCUMENTS

| | | | |
|---|---|---|---|
| 3,896,788 | 7/1975 | Sato | 128/663 |
| 4,141,347 | 2/1979 | Green et al. | 128/663 |
| 4,182,173 | 1/1980 | Papadofrangakis et al. | 128/663 X |
| 4,257,256 | 3/1981 | Yoshikawa | 73/626 |
| 4,318,413 | 3/1982 | Iinuma et al. | 128/663 X |
| 4,373,533 | 2/1983 | Iinuma | 128/663 |
| 4,407,293 | 10/1983 | Suarez, Jr. et al. | 128/660 |

OTHER PUBLICATIONS

Brandestini, M. A. et al., "BF Imaging Using a Discrete Time-Frequency Meter", 1978 UTS Sympos. Proc., Cherry Hill, N.J. (Sep. 25-27, 1978) pp. 348-352.
Skidmore, R. et al., "Maximum Frequency Follower for the Processing of Ultrasonic Doppler Shift Signals", UTS in Med. & Biol., vol. #2 pp. 145-147 Pergamon Press 1978.
Baker, D. W. "Pulsed UTS Doppler Blood Flow Sensing" IEEE Transactions on Sonics and Ultrasonics, vol. SU-17, No. 3, Jul. 1970 pp. 170-184.

Primary Examiner—Kyle L. Howell
Assistant Examiner—Francis J. Jaworski
Attorney, Agent, or Firm—Ladas & Parry

[57] ABSTRACT

Method and apparatus for ultrasonic blood flow velocity measurement based upon the doppler principle (doppler measurement), combined with simultaneous echo amplitude imaging by employing ultrasonic pulses (echo imaging). The method is used for investigation of living biological structures, in particular during movement, for example a heart function. The main application will be in hospitals and the like. The doppler measurement and the echo imaging is effected sequentially with so short intervals that the echo imaging is updated with a sufficiently high rate for obtaining an acceptable picture quality, with the doppler measurement occupying a substantial portion of the time. The information is presented in real time on a display screen. A control unit synchronizes the doppler measurement and the echo imaging, and there is incorporated one or more transducers in the equipment. The doppler measurement is interrupted during intervals which constitute a not unimportant portion of the time, for carrying out a complete or a partly sweeping of the ultrasonic beam over the image field. There is formed an estimate of the doppler signal and the estimate replaces the directly measured doppler signal either all the time or during portions of the time, for example during the interruption interval.

24 Claims, 12 Drawing Figures

METHOD OF ULTRASONICALLY MEASURING BLOOD FLOW VELOCITY

INTRODUCTION

The invention relates to a combination of ultrasonic Doppler blood velocity measurement (in the following designated "Doppler measurement") and ultrasonic echo amplitude imaging (in the following designated "amplitude imaging") obtaining for practical purposes a simultaneous imaging of a biological structure (for example blood vessel, heart ventricle, etc.) and measurement of the blood flow velocity. Techniques of Doppler measurement and amplitude imaging are regarded as prior art, and the invention relates to a method and apparatus for combining the two.

The Doppler measurements and the amplitude imaging are performed alternately during interlaced intervals, which are as short as possible but sufficiently long to complete a full scan of the ultrasonic beam over the image field for the image interval, and to obtain sufficient Doppler frequency estimation accuracy for the Doppler interval. The directly measured Doppler signal is used to generate a substitute signal that replaces the directly measured Doppler signal for audio presentation and/or spectral analysis, either all of the time or during the portions of the time when the direct Doppler signal is missing or not useful. By substitute signal we mean a signal with spectral properties close to the Doppler signal that is replaced, i.e. the signal segment that could have been obtained from direct measurement on the blood flow, and also with audible sound close to the direct signal when fed to an audio amplifier and output device.

Note that it is not necessary to estimate the actual time waveform for the missing Doppler signal. This is different from prior art [2], where attempts have been made to estimate the missing time waveform of the Doppler signal when a pulsed Doppler measurement has been interrupted for a single Doppler sampling interval to allow for the emission of a single amplitude imaging pulse.

The invention has other advantages to prior art in that:
- both pulsed wave and continuous wave Doppler measurements can be done for all practical purposes simultaneously with a real time amplitude image.
- No reduction in the pulsed wave repetition rate is necessary, avoiding any reduction in the maximum velocity that can be measured with pulsed Doppler in the combination.
- There is no reduction in the scanning rate of the ultrasonic beam over the image field during the updating of the amplitude image compared to that for a freestanding imaging instrument.

To clarify the discussion we define some concepts which will be frequently used: By direct Doppler signal we mean the audio signal obtained during direct Doppler measurements in the Doppler intervals. By substitute signal we mean the signal that replaces the direct Doppler signal. By Doppler interval we mean the time interval in which direct Doppler measurements are done. Similarly, by imaging interval we mean the time interval in which amplitude imaging is done. We normally think of the Doppler measurement being interrupted repetitively to do amplitude imaging, so by interruption interval we mean the same as the imaging interval. By substitution interval we mean the interval when the substitution signal is used.

BACKGROUND OF THE INVENTION

1. Field of the Invention

The invention relates to the field of ultrasound diagnosis of the cardiovascular systen, particular methods and devices for providing both ultrasound amplitude images and Doppler data from blood flow.

2. Relation to Prior Art

Techniques for ultrasonic blood flow velocity measurement based on the Doppler principle and echo amplitude imaging employing ultrasonic pulses are regarded as prior art, and the invention relates to a combination of these for virtually simultaneous measurements in real time. The method may be implemented by making small modifications in commercial imaging and blood velocity measuring apparati and interconnecting these through a central control unit.

The image of the biological structure is shown on a suitable display screen, and the region in which the blood flow velocity is measured is shown on the same screen. A useful spectrum analysis of the received Doppler signal may also be shown on the display and possibly printed out on a suitable printer.

The object of the invention is to simplify the aiming-in of the ultrasonic head or transducer(s) during Doppler measurement of blood velocity, by utilizing the echo amplitude image for determining the region in which the blood velocity is measured. By combining the blood velocity measurement with a dimensional measurement of blood vessels, it is possible to estimate or calculate the actual volume flow in the vessel.

A very important consideration when using equipment of the type concerned here is that the Doppler signal is presented in audible form, for example in a loudspeaker. The operator carrying out an investigation will to a high degree use the information being presented via the audio Doppler signal, in order to seek regions in the blood system in which more detailed measurement or imaging may be of interest. Therefore, it is very important that the Doppler signal presented audibly is not substantially disturbed or distorted.

Equipment for two-dimensional imaging of biological structures in real time on the basis of the amplitude of echos from a short ultrasonic pulse, is commercially available. Such known equipment is found in two versions:
- Equipment based upon sectorial scan of the ultrasonic beam which may be obtained either with a phase controlled transducer arrangement (array), or with a mechanically steerable transducer.
- Equipment based upon a linear scan of the ultrasonic beam which is obtained either with electronic selection of elements in a linear array of transducers, or with a linear mechanical movement of a single transducer. Equipment for ultrasonic Doppler measurement of blood flow velocity is also commercially available and there are two fundamental methods:
- Pulsed Wave Ultrasonic Doppler Measurement: This makes possible a depth resolution along the ultrasonic beam so that one may measure the velocity in a small region. There may also be used multi-depth sampling so that it will be possible to measure the velocity at several depths simultaneously. The pulse wave method has a disadvantage to the effect that there is a limitation of the maximum velocity which may be measured, given by the pulse rate repetition and ultrasonic frequency which is employed.

Continuous Wave Ultrasonic Doppler Measurement: With this method there will not be obtained any depth resolution along the ultrasonic beam. In exchange there is no limitation of the maximum velocity which may be measured. There are commercial instruments available which can select either pulsed wave or continuous wave operation.

There is also commercially available equipment which combines echo amplitude imaging and Doppler blood velocity measurements.

Three principles have been used:

(a) The image is frozen on the display during manual control and the ultrasonic head is utilized for Doppler measurement of blood velocity.

(b) Every second ultrasonic pulse which is emitted is utilized for Doppler velocity measurement and intermediate pulses are utilized for echo amplitude imaging. In other words, the pulses alternately serve the Doppler measurement and the amplitude imaging. This gives a simultaneous measurement of Doppler frequency and amplitude image in real time at the cost of reduced pulse repetition frequency for the Doppler instrument [1].

(c) Finally there is a design in which several Doppler pulses are emitted as a contiguous train having repetitive interruptions for a single echo amplitude imaging pulse, for example after every tenth Doppler pulse [2].

The above methods of interrelating amplitude imaging and Doppler measurement have deficiencies and disadvantages as follows:

(i) With the frozen image, movements of the measuring head or the object of measurement when the image is frozen, will give faulty indications of the region in which the velocity is measured.

(ii) With alternate emission of Doppler and imaging pulses, the emission rate of the Doppler pulses will be reduced so that the maximum velocity which may be measured, is reduced.

(iii) With the third method it is difficult to avoid the disturbance that the imaging pulse causes in the Doppler signal. To reduce this disturbance, the pulse repetition rate of the amplitude imaging must be kept as low as possible, which in practice will give a slowly sweeping update of the amplitude image. The frame rate of the imaging also becomes low. This is confusing, especially with moving objects like the heart. The artifacts in the audio signal due to the imaging pulses are annoying for the operator, and make it makes it difficult to use that signal for guidance.

In methods (b) and (c) a continuous wave Doppler measurement may not be used, which means that the maximum velocities which may be measured are determined by the pulse repetition frequency in the Doppler pulse mode.

These deficiencies are avoided with the present invention by:

1. Performing Doppler measurements and amplitude imaging alternately during interlaced intervals, with the imaging intervals long enough so that a complete image scan can be done and the Doppler intervals at least long enough to obtain sufficient accuracy of the Doppler frequency estimate.

2. Using a substitute signal that only approximates the spectral properties and the audio sound of the Doppler signal instead of the time waveform of the Doppler signal. This allows for interruption of the Doppler measurement for imaging intervals that are longer than the correlation time of the Doppler signal, so that a complete sweep of the ultrasonic beam can be done.

3. Using the signal after the tissue filters of the Doppler instrument, whereby the strong signal component from tissue structures are removed, as the basis to generate the substitute signal, resulting in a more robust estimate.

The large interrupt interval for amplitude imaging allows for the same scan rate of the ultrasonic beam over the image field as for dedicated imaging. Structures in different parts of the field are then imaged during such a short interval that physiological movement are practically "frozen" during the sweep, and the artifacts due to slow sweep rate for method "c" above are avoided. Also, the Doppler interval can be kept small so that a high frame rate of fully updated images occurs (typ. 20 frames pr sec.). Moreover, both pulsed and continuous wave Doppler measurements can be done during the Doppler interval, and the pulse rate in pulsed mode need not be reduced from what it is for a dedicated Doppler device. Thus the maximum velocity that can be measured is the same as for a freestanding pulsed and continuous wave Doppler in contrast to methods (b) and (c) above.

The substitute signal replaces the directly measured Doppler signal either all of the time or during those portions of the time when the direct signal is not available due to the imaging, and also due to ringing in the tissue filters of the Doppler instrument as discussed below. When the intervals for direct Doppler measurements are much shorter than the intervals when Doppler measurements are interrupted for imaging, it is best to use the substitute signal all of the time. The direct Doppler signal is then used to update the generator for the substitute signal. When the Doppler intervals are comparable or longer than the imaging intervals, and the imaging intervals are not too long (approx. 20 msec.), better overall quality of the audible signal is obtained when substitution is done only when there is no direct Doppler signal available. The quality of the composite signal then generally improves the longer the Doppler interval is, but the frame rate reduces as the length of the Doppler interval increases. Good performance is obtained with an imaging interval of 17 msec and a Doppler interval of 50 msec, giving a total frame time of 67 msec and a frame rate of 15 frames pr sec.

The techniques for obtaining approximate values for signals that are not measured completely are in technical literature called estimation techniques. This concept covers both smoothing of data to remove noise (filtering), estimating values in between measured data values (interpolation), and generation of future data (prediction). The substitute signal described in this patent can be obtained through estimation schemes, but it is important to note that it is not a requirement that the substitute signal be an approximation to the time waveform of the direct Doppler signal; it is only necessary that it has comparable spectral properties and thereby, audible sound, to the signal being gated out. This is sufficient for the use, and gives a simpler estimation scheme than that for estimating the time waveform, since the substitution interval in practical applications is far longer than the correlation time of the Doppler signal. For illustration, a commonly used method for signal waveform prediction is a linear minimum variance predictor. This will give a predicted value equal to the signal mean value (which is zero in this case) for time intervals which are larger than the correlation time of the direct Doppler signal.

There is a fundamental difference between pulse echo amplitude imaging and Doppler measurement of velocity, in that with amplitude imaging, only one pulse is needed in each beam direction to collect the data. For Doppler measurements one must measure over a longer period to estimate the Doppler shift in frequency with sufficient accuracy. Assume that we do Doppler measurement for an interval T. The accuracy in the estimate of the Doppler shift, Df, is then $Df = 1/T$.

Typically we use T > 2 msec which gives Df < 500 Hz. For amplitude imaging in comparison, the time to collect data for one beam direction is on the order of 200 $\mu$sec, i.e. 1/10th of what is needed for Doppler measurements. Thus the imaging portion of the instrument can be rapidly switched on and off without interfering significantly with the measurement, while Doppler measurements must be continuous for a longer period to obtain accuracy.

To this point we have not been fully clear about what we mean by Doppler signal, illuding to tha it is the audio signal obtained during Doppler measurements. Existing Doppler instrumants contain mixercircuits which transfers the received rf-signal either down to base-band, generating two audio quadrature signals to maintain direction of blood flow, or centers the signal around an audio offset frequency. The signal is then fed through filters (high-pass filters for the base-band system, and band-reject filters for the off-set system) to remove strong, low Doppler shift signal components from tissue structers. We call these tissue filters in the following.

One reason to bring the signal down to the audio region is that simpler circuits may be used for analysis, but in principle we might as well do the tissue filtering and further analysis at rf-frequencies. The present invention does not specify at what level the signal processing is done, but is clearly simplest to do it with base-band system.

When switching the Doppler instrument on and off, there will be strong transient ringing in these tissue-filters due to the abrupt excitation at the input of these filters. The Doppler signal will not be useful during this ringing period which lasts on the order of milliseconds. Another way to view this is that some time of measurement is necessary in order to estimate the low frequency components with sufficient accuracy so that they can be removed from the signal.

It is difficult to obtain high quality blood flow Doppler information if one tries to predict or interpolate a missing part of the Doppler signal (due to an imaging interrupt) prior to any tissue filtering, since this signal is comprised of components from both tissue and blood. The Doppler signal from blood is much weaker than the low Doppler shift signal from the tissue structures (typically more than 60 dB weaker), such that even a small fractional error in the estimate will have amplitude comparable to the signal from blood. For example, with a 60 dB ratio, a fractional error of 0.1% in the estimate will give an error comparable to the amplitude of the signal component from blood. This is the reason why the imaging pulses cause strong disturbances in the audio signal when using the method cited under "c" above. In this method, a pulsed wave Doppler measurement is interrupted repetitively for one pulse at a time, to generate a single amplitude imaging pulse and then substitute the lacking Doppler sample with an estimated value, without any prior tissue filtering. As estimate it is suggested to use either the previous Doppler sample or a linear combination of the previous and the following Doppler samples. Both these estimators have so large errors that they give a strong disturbance to the Doppler signal from blood, and it seems difficult to find practical estimators that will not have the same deficiencies. Because of this disturbance, the imaging pulse rate has to be reduced which is responcible for the slow sweeping image update of this method.

The present invention avoids this problem by using the Doppler signal from blood, after the low frequencies from tissue have been removed by tissue filtering, as the basis to generate a substitute signal. By that, the strong echos from tissuse structures have been removed, and the substitute signal has approximately the same amplitude as the Doppler signal from the blood. Therefore a fairly large relative estimation error can be tolerated and still give a small amplitude disturbance relative to the Doppler signal from the blood. Also, since according to the present invention we are only concerned with the spectral properties of the substitute signal, the estimation procedure is more robust than if we were to estimate the time wave form of the Doppler signal. It should also be noted that if we use the signal after the tissue filter as a basis for the estimation, the interruption of the Doppler measurement has to be longer than the transient ringing of the tissue filter, since the ringing disturbs the Doppler signal from the blood. This ringing time is normally larger than the correlation time of the Doppler signal, and it is then difficult to estimate the time waveform of the missing Doppler signal after the tissue filter, as discussed above. Therefore, using a substitution signal as in the present invention, has great advantages.

SUMMARY OF THE INVENTION

On the background of known techniques this invention takes as a starting-point known methods of ultrasonic blood flow velocity measurement based upon the Doppler principle (Doppler measurement), and known methods of real time echo amplitude imaging employing ultrasonic pulses (amplitude imaging), for investigating living biological structures, in particular during movement, for example a heart function, said Doppler measurement and said amplitude imaging being effected alternately over sequential time intervals, each interval for amplitude imaging being sufficiently long to complete a full scan of the ultrasonic beam over the image field so that a complete update of the amplitude image is generated, and each interval for Doppler measurements being sufficiently long to obtain the required accuracy in the Doppler frequency estimate whereby image information from the amplitude imaging and an indication of the measurement region for the Doppler measurement is presented in real time on a display device, and in which a control unit serves to synchronize the Doppler measurement and the amplitude imaging, one or more transducers being activated at any given instant for carrying out either Doppler measurement or amplitude imaging. What is novel and specific in the method according to the invention primarily consists therein that the Doppler measurement is interrupted during intervals, for carrying out a complete or substantial fraction of a scan of the ultrasonic beam over the image field to generate the amplitude image, and that the directly measured Doppler signal is used to generate a substitute signal which replaces the directly measured Doppler signal either all of the time or during the portions of the time when the directly measured Doppler signal can not be used or is missing. Other specific features according to the invention appear from the claims, and the invention also comprises an apparatus for carrying out the method.

BRIEF DESCRIPTION OF THE DRAWINGS

The invention shall be explained more closely in the following description with reference to the drawings, in which.

DETAILED DESCRIPTION OF THE INVENTION

The invention relates in specific to a method of combining an ultrasonic Doppler measurement and pulse echo amplitude imaging measurement for apparant simultaneous operation of the two in real time, and also an apparatus with means of carrying out the method. Essential to the invention is that both pulsed and continuous wave Doppler measurements can be used without reducing the maximum velocity that can be measured compared to that for a freestanding pulsed and continuous wave Doppler device, and that a complete or substantial fraction of a scan of the ultrasound beam over the image field can be accomplished without interruption so that the update scanning rate of the amplitude image is not reduced from what it is for a freestanding imaging device, and the updating of the image appears instantaneous on the display without noticable sweeping artifacts. It is also essential that the Doppler signal can be presented audibly with little disturbance from the amplitude imaging.

In order to obtain this, interlaced operation between Doppler measurements and amplitude imaging is used, forming a substitute signal on the basis of directly measured Doppler signal either all of the time or in the intervals when the direct signal is missing or has poor quality due to for instance ringing in the tissue filters in the Doppler instrument.

The method can be implemented in many ways, for example using the same transducers for Doppler measurements and amplitude imaging, separate transducers for the two, both electronic and mechanical steering of the ultrasonic beam, using different kinds of display devices and methods of spectrum analysis for the Doppler signals, etc. Some of the descriptions given are therefore incomplete concerning details since it is obvious to one skilled in the art how to add the details so that the invention may be practiced. Also, some of the implementations shown must be regarded as examples and it is obvious that different examples of implementations may be given by someone skilled in the art.

Figure 1:
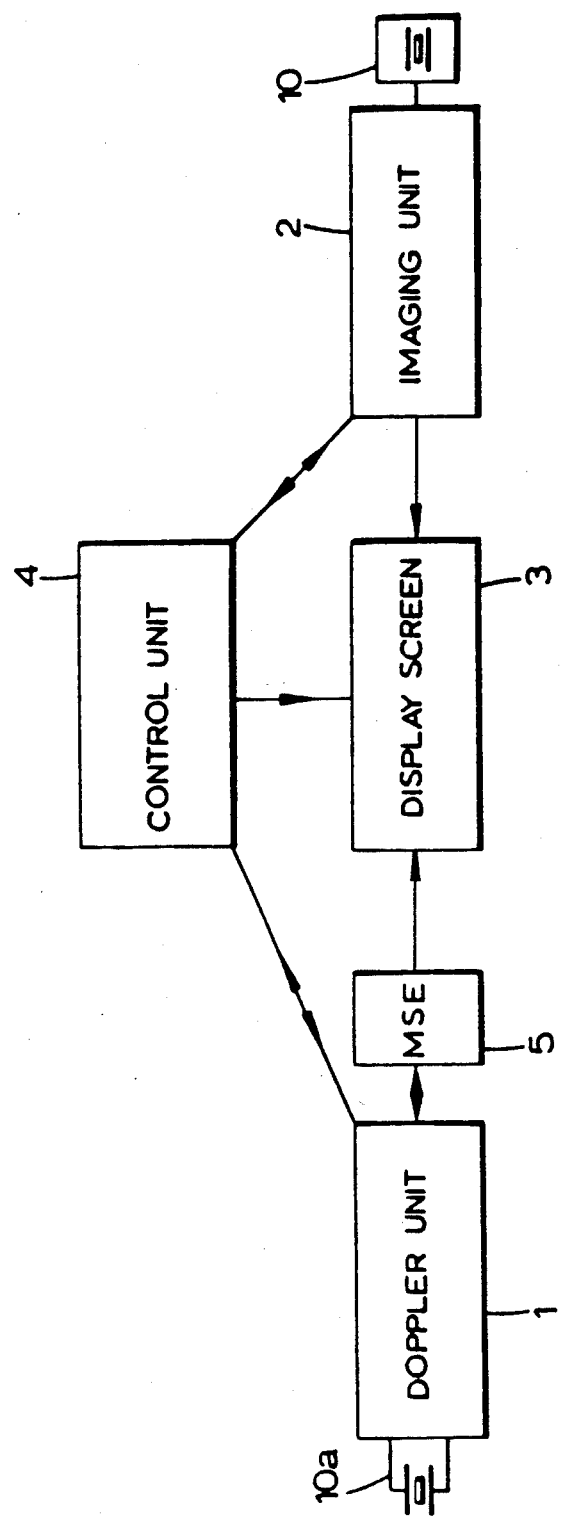
FIG. 1 is a block diagram of an apparatus for carrying out the method according to the invention, FIG. 2 schematically shows a form of image presentation by means of an apparatus according to the invention, FIG. 3 schematically shows a second form of image presentation by means of an apparatus according to the invention, FIG. 4 schematically shows a modification of the arrangement in FIG. 2 with a separate Doppler transducer.

FIG. 1 shows a block diagram of an apparatus for practical implementation of the method according to the invention. The apparatus consists of a central control unit 4, an echo amplitude imaging unit 2 for two-dimensional amplitude imaging in real time, a Doppler unit 1 with an associated unit 5 designated MSE (Missing Signal Estimator), as well as equipment, for example a cathode ray tube screen 3, for suitable display and presentation of the image and the Doppler spectrum. The method may be correspondingly utilized in one-dimensional and three dimensional echo amplitude imaging.

Both the Doppler unit 1 and the imaging unit 2 may be switched on and off electronically. Both units are controlled by the control unit 4 which operates according to established principles for such control. During operation the control unit 4 provides for interruptions in Doppler measurement during short time intervals (for example 15 msec.) in order to carry out a complete scan of the ultrasonic beam over the image field. The directly measured Doppler signal is used to generate a substitute signal which replaces the direct Doppler signal either all of the time or during portions of the time when the direct Doppler signal is missing, or cannot be used, for example due to the image interruption intervals, and transients in the tissue filters. The substitute signal is generated by MSE-unit 5.

The echo amplitude image which is produced during each image sweep of the beam is stored in a suitable electronic image memory which is continuously scanned for presentation of the image on the display screen. Such storage methods are in use in several commercial instruments. The control unit 4 provides for the time organization of the Doppler measurement and the amplitude imaging measurement as well as the transmission of the signals for a suitable display and print-out. These vary in detail according to which Doppler and imaging units are used, and may be designed on the basis of the same techniques as in control units found in other time sequential instruments.

In FIG. 1 there is also schematically shown a Doppler transducer 10a and a transducer array 10 for the amplitude imaging, which for example may correspond to what is illustrated in somewhat more detail in FIG. 4 or in FIG. 5 which is to be explained in the following.

Figure 2:
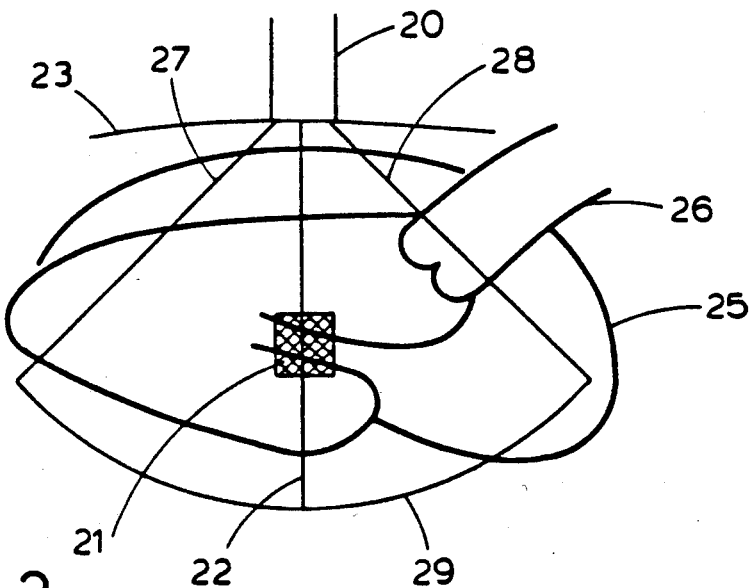

The same transducer may be used both for imaging and Doppler measurements by switching it to the actual unit using relays or electronic switching in synchronism with the activation of the unit, for example as indicated in FIG. 2 for a phased array transducer. Similar switching can be used with a mechanically steered transducer.

The function of the apparatus in FIG. 1 shall be explained more closely below, in particular with reference to FIGS. 6–9.

Figure 3:
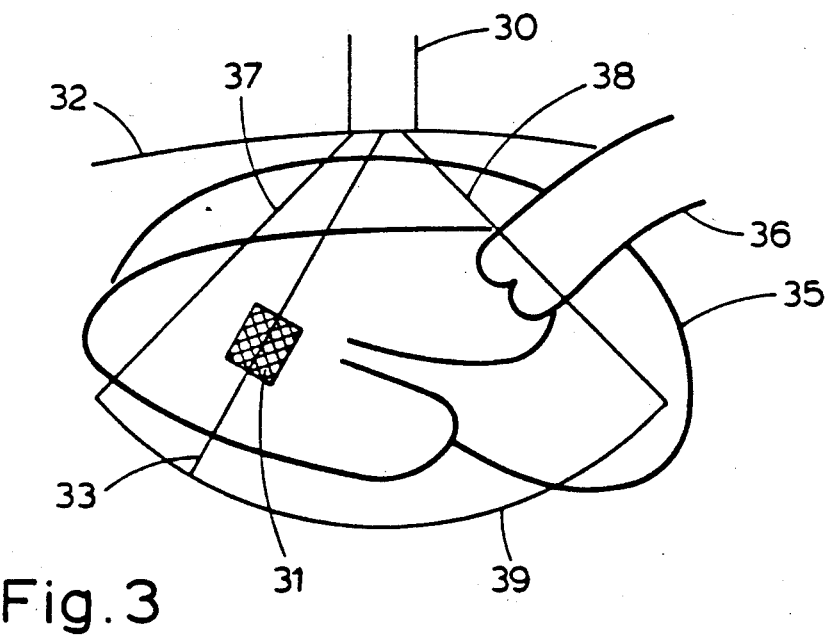

FIGS. 2 and 3 indicate two examples of image presentations and indication of the region 21 (FIG. 2) and 31, resp. (FIG. 3), in which the blood velocity is measured with a pulsed wave Doppler using a phase controlled transducer array. For continuous wave Doppler measurements, the region of observation is determined by the overlap region between the transmitting and receiving transducer beams. Since these normally overlap along the whole beam, a line symbolizing the beam direction would then be sufficient to indicate the measurement region on the display.

In the figures there is indicated a heart 25 and 35, resp., with aorta 26 and 36 resp., as well as the extension of the image field by means of lines 27, 28, 29, and 37, 38, 39 resp. The skin of the patient is shown at 23 and 32 resp.

The same ultrasonic head 20 and 30 resp., is used for both Doppler measurement and amplitude imaging. In FIG. 2 the ultrasonic beam 22 for the Doppler measurement (Doppler beam) is directed normal to the transducer face. In this case it is possible with suitable selectors (either relays or electronic switches) to interconnect several elements in the transducer array into a single Doppler transducer.

In FIG. 3 the direction 33 of the Doppler beam is deviated from the center line. In order to obtain this, the signal must be phase controlled in all transducer elements 30, for example by means of the same electronics which is used for phase control during imaging. The method according to FIG. 2 results in a better sensitivity in the case of inaccurate or noisy phase control electronics.

Figure 4:
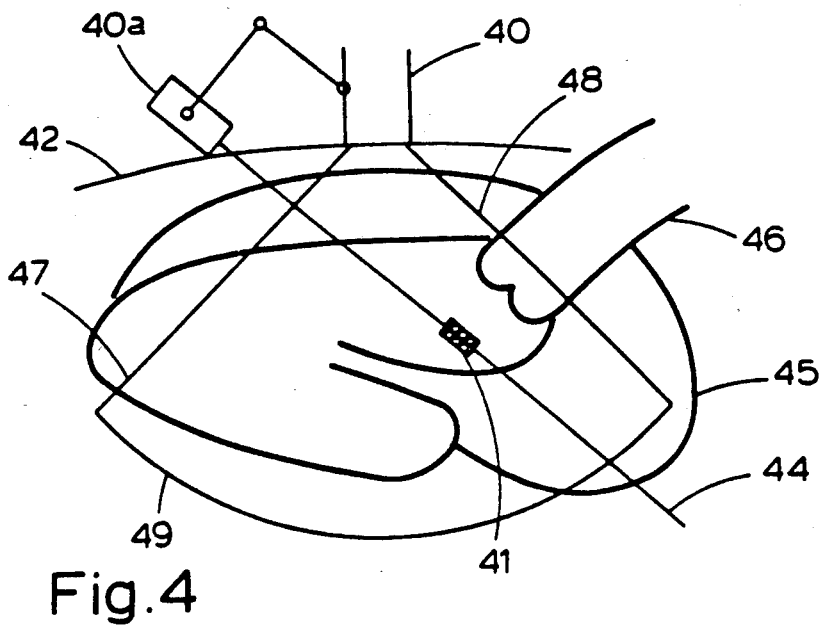
Figure 5:
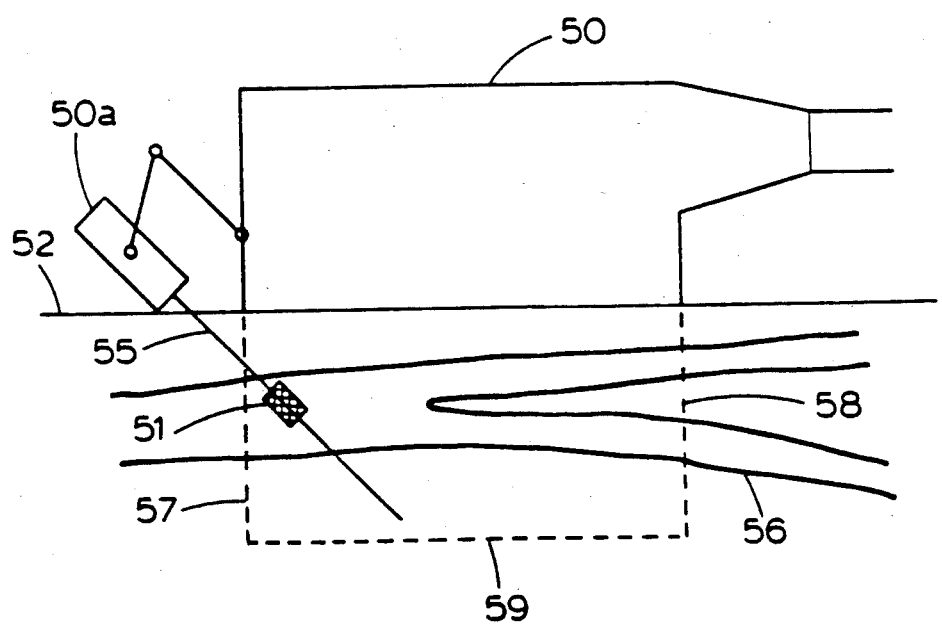
FIG. 5 shows still another form of presentation based on the use of a linear transducer arrangement (array) for the echo imaging and a separate Doppler transducer.

There may also be employed a separate transducer 40a for the Doppler measurements as illustrated in FIG. 4, in which a transducer array 40 serves for amplitude imaging by sectorial sweeping within limitation lines 47, 48. FIG. 5 shows linear image sweep by means of a linear transducer array 50 and with a separate Doppler transducer 50a. The transducers 50 and 50a are shown in contact with the skin 52 of the patient, with an indication of a blood vessel 56 underneath, this vessel being in part located in the image field or region which is limited by the lines 57, 58, and 59. The measurement region 51 for the Doppler measurement is shown within the vessel 56.

This arrangement with a separate Doppler transducer has the advantage that the Doppler transducer 50a may be optimized for better sensitivity in Doppler measurements. With a mechanical imaging sweep there may be employed a separate stationary Doppler transducer, as in 40a and 50a, if it is difficult to arrest the movable imaging transducer sufficiently quickly for Doppler measurements.

Figure 9:
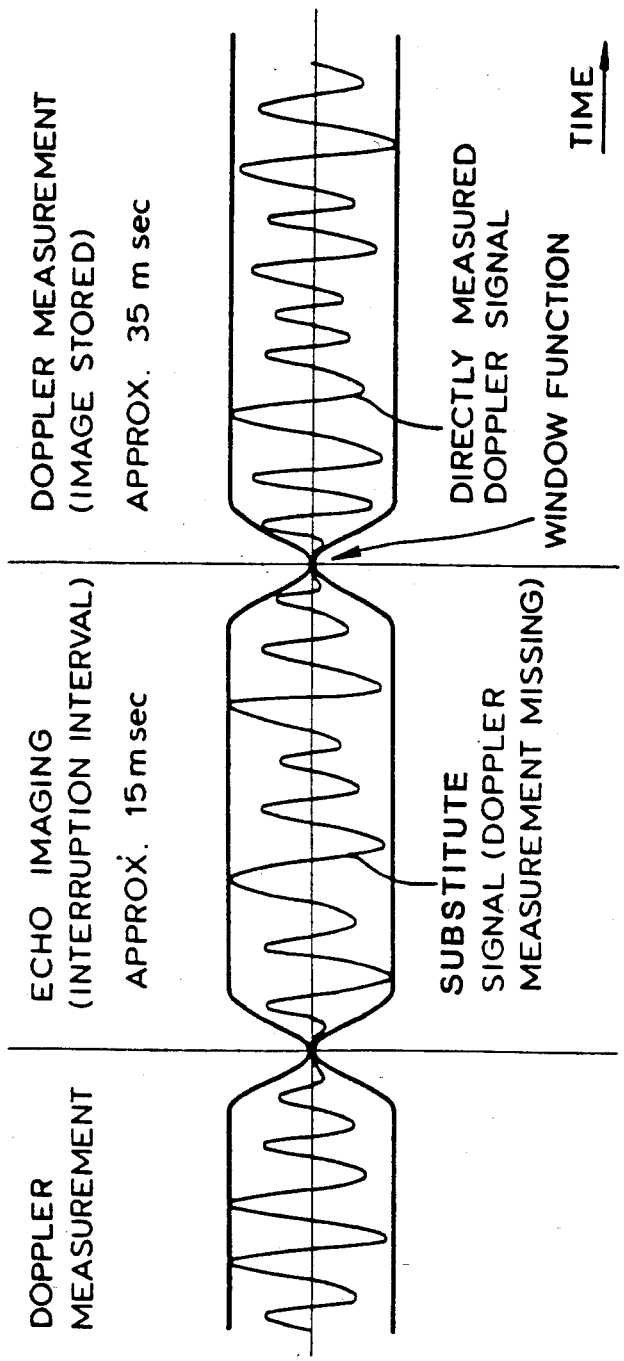

At this point reference is made to FIG. 9, which in the first place shows an example of time sharing between echo imaging and Doppler measurement of blood activity. The interruption interval is sufficiently long to scan the ultrasonic beam over the whole image field so that the rapid update of the amplitude image is obtained. With the time intervals indicated in the figure there will be an image repetition period of 15 msec + 35 msec = 50 msec, giving 20 frames per second. By reducing the Doppler time from 35 msec to 18 msec, for example, the repetition period is reduced to 15 msec + 18 msec = 33 msec, increasing the frame rate to 30 frames per second.

One should note that during the amplitude imaging time in the interruption interval, several ultrasound pulses are emitted so that the whole image field is scanned. The length of this interval is therefore determined by the depth of the image field in conjunction with the number of ultrasound lines wanted in the image. The length of the Doppler interval is determined from the quality requirement of the overall Doppler signal, both the direct Doppler signal and the substitute signal. In the figure it is shown replacement with a substitution signal only during an interruption interval for amplitude imaging, while, according to the invention, substitution can also be done during all of the time, using the directly measured Doppler signal to update the signal estimator. This latter approach is useful when the interval for Doppler measurement is much shorter than the imaging interval.

Figure 6:
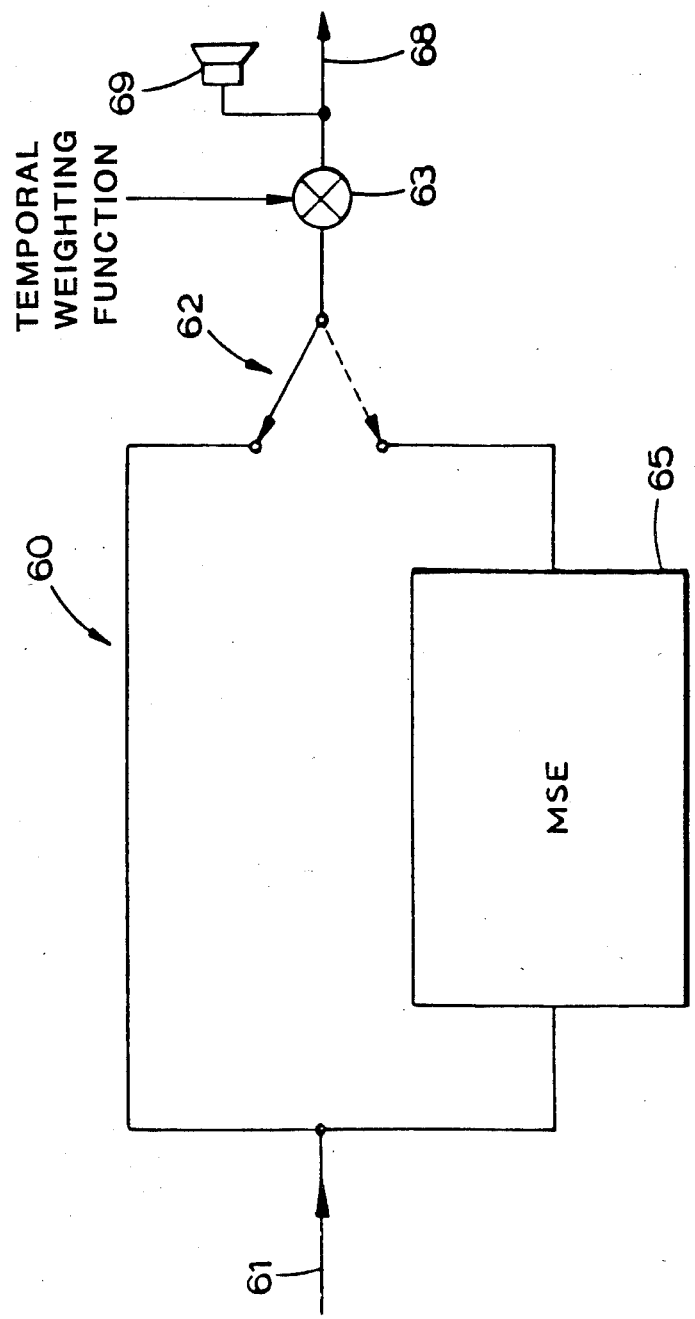
FIG. 6 illustrates that part of the apparatus in which the directly measured Doppler signal is replaced by a substitute signal, FIG. 7 schematically shows an embodiment for forming a substitute signal for the Doppler signal, FIG. 8 schematically shows another embodiment to generate a substitute signal, FIG. 9 schematically shows an example of the time division between amplitude imaging and Doppler measurement and, besides, a certain signal processing (temporal weighting)
Figure 7:
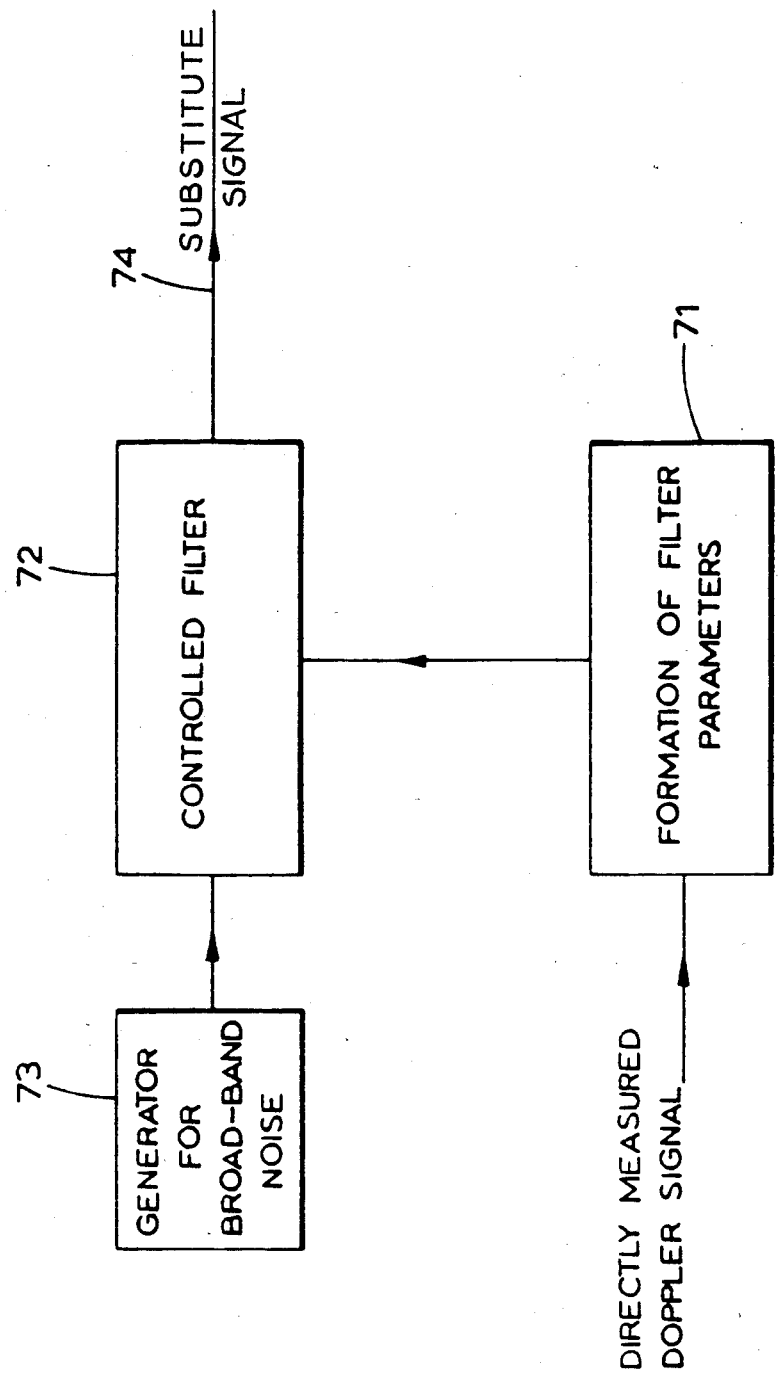

As mentioned earlier, the directly measured Doppler signal is used to generate a substitute signal which replaces the direct Doppler signal either all of the time or when there is a lack of direct Doppler signal. In FIG. 6 a method for switching between the directly measured Doppler signal and the substitute signal is illustrated. Switch 62 is used to select either the direct Doppler signal 61 or the output of the MSE-unit 65. In the upper position of the switch (solid arrow) there is a direct connection from 61 to 63 through 60, and in the lower position of the switch 62 (dashed arrow) the output of the MSE-unit is connected to 63. The proper signal is thus passed to the following parts of the apparatus for an audio presentation and spectral analysis and display. If the apparatus, according to the general idea behind the invention, is using the substitute signal all of the time, the switch 62 will be permanently in its lower position, or may be eliminated by providing a signal path which goes through MSE-unit 65. When the switch 62 is present, it is possible by suitable control thereof to select those portions of the time during which the substitute signal shall replace the directly measured Doppler signal.

The substitute signal is generated in the MSE-unit 65 corresponding to the unit 5 in FIG. 1, on the basis of the properties of the directly measured Doppler signal, for example before and/or after the interval when interruption of Doppler measurement is done to do amplitude imaging. Estimation of the substitution signal may, for example, be effected in the following ways:

(a) On the basis of the properties of the Doppler signal, for example immediately prior to an interrupt for amplitude imaging, there may be generated a substitute signal by applying a broadband signal to a controlled filter 72 and a device 71 which serves to form filter parameter signals which control the instantaneous filter characteristics of the filter 72. The filter may for example be designed as a transversal filter in which the tapping weights are adjusted in order to obtain the spectrum desired.

Figure 8:
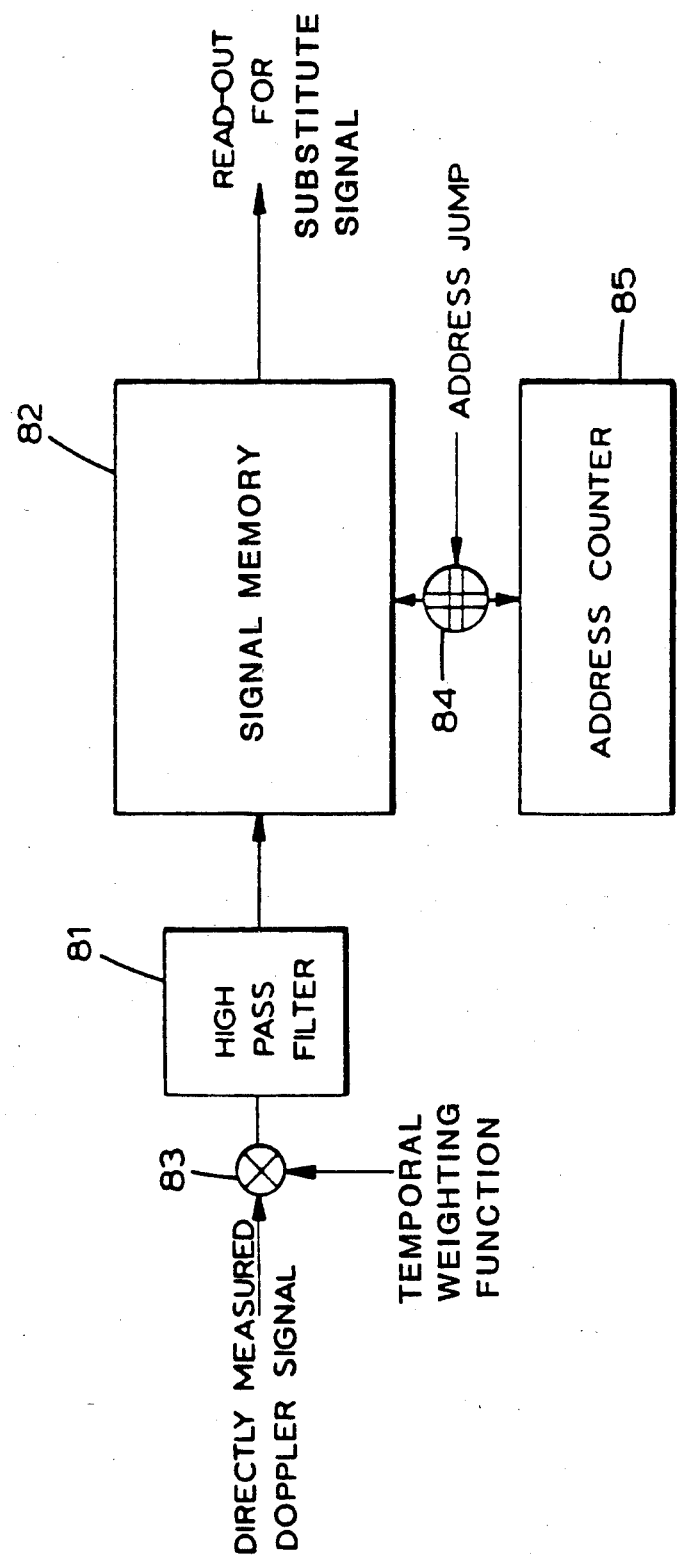

(b) According to FIG. 8 the directly measured Doppler signal may be stored continuously, for example in a digital memory 82 by the control of an address counter and an address jump control at 84. When an interruption is made for amplitude imaging, the address jump is used so that the last part of the stored signal may be read out and utilized as a substitute signal during the imaging period.

In the embodiment of FIG. 8 units 82, 84, and 85 may be considered to constitute a MSE-unit 5 as shown in FIG. 1. In a corresponding way the above embodiment in FIG. 7 comprises units 71, 72, and 73 which may be considered to constitute a MSE-unit. The "directly measured" Doppler signal at 61 in FIG. 6 has been passed through a tissue filter, for example a filter 81 as shown in FIG. 8. In the case of pulse Doppler measurement there can be an interpolation low pass filter in front of or after the tissue filter. These filters are prior art knowlege for ordinary Doppler instruments.

In order to obtain a smooth transition between the substitute signal and the directly measured Doppler signal, there may be carried out a multiplication of the signal by a temporal weighting function as indicated at 63 in FIG. 6. With this method the signal level is gradually reduced to zero before switching over, and is again gradually increased to the full magnitude after switching over. This is illustrated in FIG. 9 which shows how the signal levels may vary at the transition from direct Doppler signal to substitute signal and vice versa. There may also be provided for an overlap between the directly measured Doppler signal and the substitute signal, by starting to increase the level of the substitute signal, while reducing the level of the direct signal. At the transition from the substitute signal to the direct signal, an increase in the level of the direct signal is initiated whereas the level of the substitute signal is being reduced.

Figure 10:
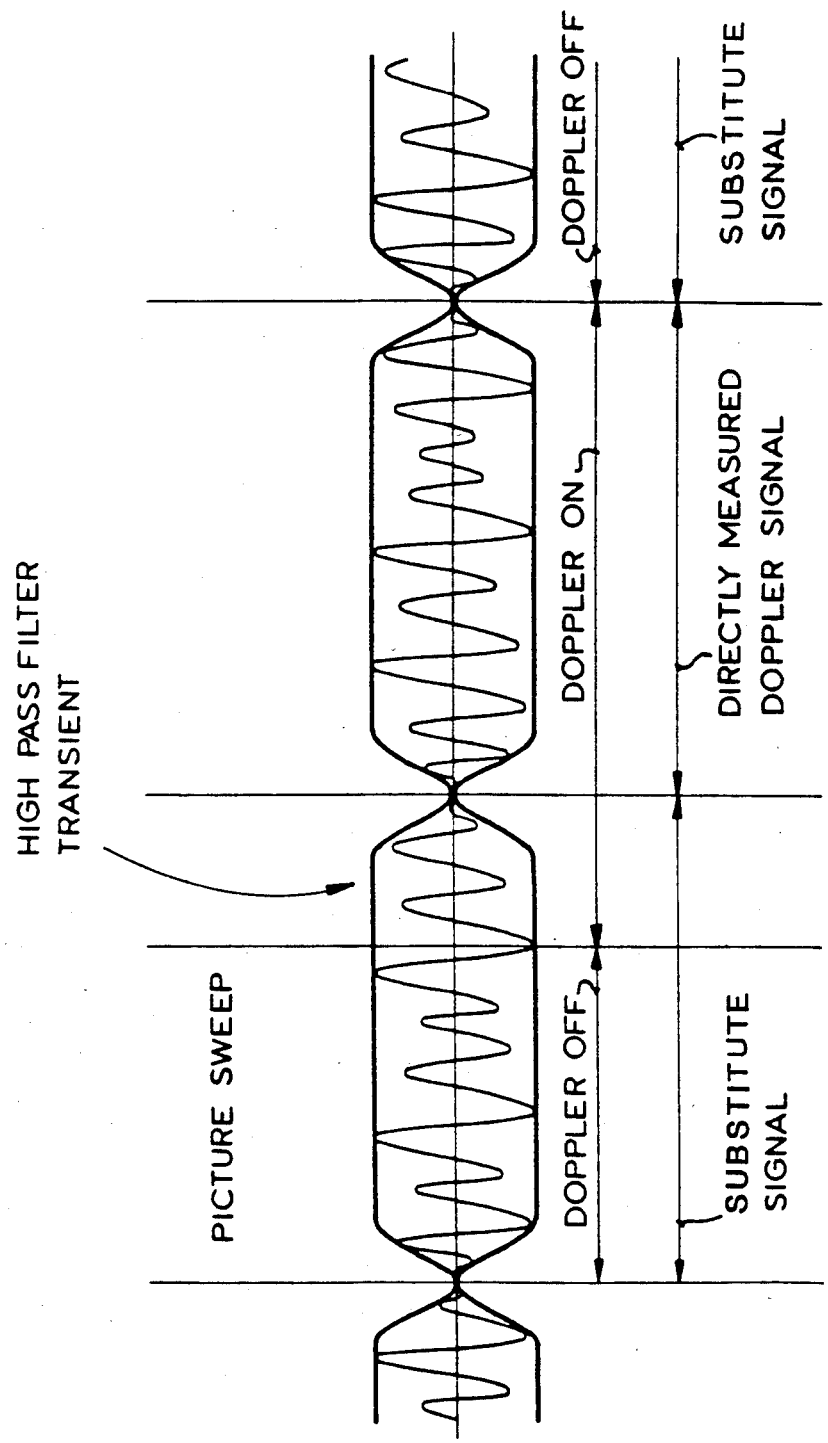
FIG. 10 shows a time diagram similar to the one shown in FIG. 9, but in a particular embodiment to be used with a tissue filter.

In order to supress strong reflections from tissue boundaries in the biological structure, the Doppler instrument is provided with a tissue filter 81 (FIG. 8) having rapid roll off from pass band to stop band. When commencing the Doppler measurement after the imaging period (the interruption interval), there will be transients in the tissue filter. The directly measured Doppler signal will not be useful in the transient period of the tissue filter, and therefore the substitute signal must be used also during this period. Accordingly the substitute period will be longer that the image scanning period as illustrated in FIG. 10.

The transient time of the tissue filter may be reduced by multiplying the signal in front of the filter by a temporal weighting function as shown at 83 in FIG. 8. The signal level in front of the filter 81 is then slowly increased from zero to its full level. A reduction of the transient time in the tissue filter may also be obtained by changing the frequency response of the filter during the transient time.

Figure 11:
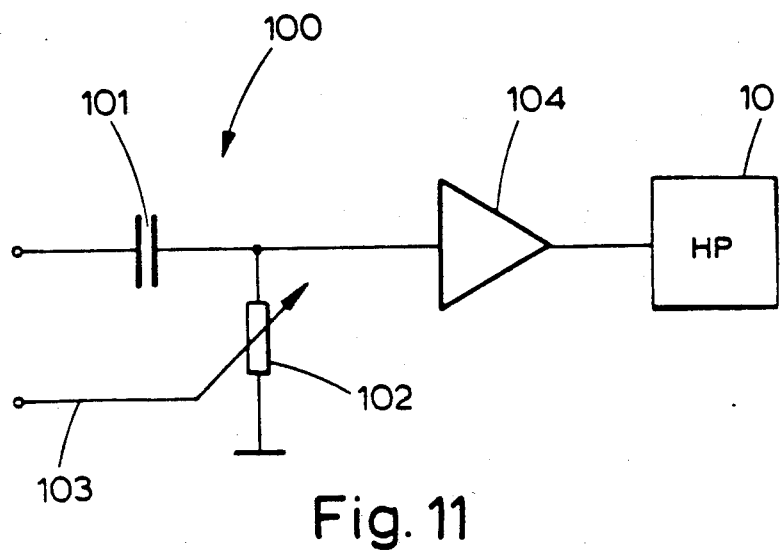
FIG. 11 is an example of a prefiltering network to be arranged in front of the tissue filter in the apparatus.

An example of a pre-filtering network 100 which does this, is shown in FIG. 11, in which there is incorporated a voltage controlled resistor 102 with a control signal input 103. When the Doppler measurement starts, the value of the controlled resistor 102 is very low or approximately equal to zero ohms, which results in low amplification and a high cut-off frequency of the filter 100. The value of the controlled resistor 102 is then increased to its maximum value during a time interval comparable to the transient time of the tissue filter after the switching-on of the Doppler instrument after the image sweep.

Besides, in FIG. 11 there is in addition to the actual prefiltering network consisting of capacitor 101 and the controlled resistor 102, shown a buffer amplifier 104 between the prefiltering network and the actual tissue filter 105, the transient time of which is to be reduced. The prefiltering network may be incorporated as a part of the high pass filter. It is also possible that in the prefiltering network 100 in FIG. 11 the capacitor 101 could have been a voltage controlled capacitor, and controlled instead of the resistor 102, or possibly both of these components could be of the voltage control type. What is essential here is that the described change in characteristics of the prefiltering network is obtained during the transient time of the tissue filter.

Figure 12:
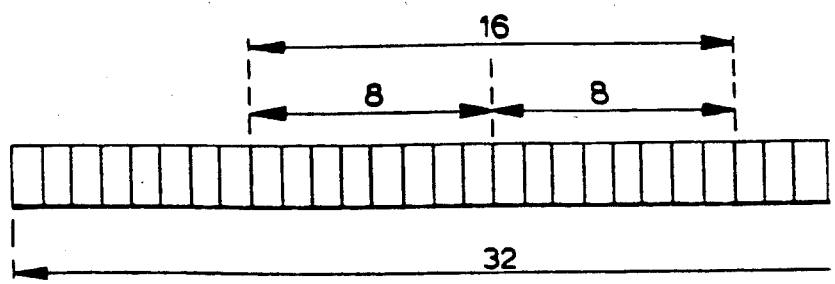
FIG. 12 shows an example of a transducer arangement (array) for use in the apparatus according to the invention.

FIG. 12 shows a preferred transducer arrangement (array) for use in the apparatus according to the invention, this arrangement being of particular interest in connection with the embodiment of FIG. 2. As shown in the example of FIG. 12 there is a number of transducer elements located along a line. The central 16 elements or possibly all the elements, are used connected together for pulsed wave Doppler measurement. This is provided for by electronic switching or possibly by means of relays in a manner known per se. In the continuous wave mode of the Doppler measurement half of the elements are used to transmit the ultrasound and half of the elements are used to receive the backscattered ultrasound.

During amplitude imaging the total number of transducer elements will operate under a phase delay control being known per se. It is obvious that the arrangement may have other numbers of transducers than the 32 transducers shown in FIG. 12.

Finally, it shall be mentioned that the ratio of the time intervals for Doppler measurement and amplitude imaging, respectively, may be different from what is discussed with reference to FIGS. 9 and 10. Thus, depending upon the accuracy desired in the determination of velocity, the Doppler measurement may occupy a smaller portion of the time than the imaging (the interruption interval).

REFERENCES

[1] U.S. Pat. No. 4,373,533 Iinuma et al.
[2] U.S. Pat. No. 4,407,293 Suarez et al.

We claim:

1. A method of ultrasonically measuring the blood flow velocity by combining ultrasonic Doppler blood velocity measurements, either pulsed wave or continuous wave, and pulse echo amplitude imaging by measuring scan lines to enact an imaging sweep for investigating biological systems, the steps comprising, alternately carrying out said Doppler measurement and said amplitude imaging sweep during sequential time intervals with such rapid alteration that the Doppler measurement and amplitude imaging appear simultaneous to a usser, providing sufficiently long time intervals for each amplitude imaging sweep for acquiring a plurality of scan lines of an ultrasonic beam over an image field so that the scanning appears instantaneous to the user without any reduction from the image scanning rate for a freestanding imaging instrument, providing time intervals for either a continuous wave Doppler measurement or for several ultrasonic pulses for pulsed Doppler measurements, the minimum length of each time interval being sufficiently long to obtain a Doppler frequency estimation to generate a substitute signal, presenting said amplitude imaging together with an indication of the region of Doppler measurement in real time on a display device, the region of Doppler measurement consisting of a small and localized region for pulsed wave measurements or comprising the region of the overlap between transmitting and receiving beams for continuous wave Doppler measurement, generating a substitute signal with spectral content close to that of the Doppler measurement, said substitute signal being generated from the Doppler measurement after passing through a tissue filter removing strong low frequency components from tissue structures, said substitute signal replacing said Doppler measurement at least when there is no useful Doppler measurement present, presenting the resulting signal in an output form providing a close approximation to that of a simultaneous Doppler measurement, either pulsed or continuous wave, and amplitude imaging without any a freestanding Doppler instrument or without any reduction in the beam scanning rate for updating an amplitude image produced solely by a free-standing imaging instrument.

2. In a method according to claim 1, further comprising the step of forming the estimation during each estimation interval on the basis of a doppler signal curve during a certain time associated with each said estimation interval, said estimation replacing the Doppler measurement during the interruption interval.

3. In a method according to claim 2, further comprising the step of forming the estimation by continuous storing of the doppler signal in a store, and reading that part of the doppler signal last stored out of the store and using said part as the estimate during each interruption interval.

4. In a method according to claim 1, further comprising adjusting the instantaneous filter characteristic of a controlled filter on the basis of the characteristic of said Doppler measurement, for example the power spectrum thereof, and supplying the controlled filter with broadband noise so that the filter output delivers an estimate of the Doppler Measurement.

5. In a method according to claim 1, further comprising the steps of selecting between pulse or continuous wave Doppler modes, the selection between continuous or pulse mode doppler measurement taking place independently of the echo imaging and providing a pulse rate in the case of pulse mode doppler measurement which is independent of the pulse rate for the echo imaging.

6. In a method according to claim 1, further comprising the step of introducing said estimate in the signal path after the tissue filter.

7. In a method according to claim 6, further comprising the step of changing the tissue filter characteristic after the termination of each estimation interval during an interval of the same order of magnitude as the transient time of the tissue filter, from an increased cut-off frequency to a lower cut-off frequency.

8. In a method according to claim 7, said changing step including the step of effecting changing of the tissue filter characteristic in a prefiltering network comprising a series capacitor and a parallel resistor, wherein the capacitor or the resistor or both are voltage controllable and supplied with a control voltage thereby providing for the change of the filter characteristic.

9. In a method according to claim 6, including the step of introducing a window function in front of the tissue filter for reducing the transient time in the tissue filter.

10. In a method according to claim 6, further including the step of providing for an adjustment or smoothing of the Doppler measurement or the estimate signal at the transitions between the Doppler measurement and the estimate, in particular at the termination of the estimate time.

11. In a method according to claim 10, wherein said smoothing step includes the step of effecting the smoothing of the signal or the signals is effected by multiplication with a suitable window function, for example a cosine function.

12. A method according to claim 1, further comprising the step of presenting said resulting signal in audible form.

13. An apparatus for combined ultrasonic Doppler blood velocity measurements, either pulsed wave or continuous wave modes, and pulse echo amplitude imaging, for investigating biological systems, where Doppler measurement and said amplitude imaging are alternately carried out during sequential time intervals with such rapid alternation that the Doppler measurement and amplitude imaging appear simultaneous to the user, each time interval for the amplitude imaging sweep being sufficiently long for a complete or significant fraction of a complete sweep of the beam over the image field so that the scanning rate of the ultrasonic beam over the image field appears instantaneous to the user without any reduction from what it is for a freestanding imaging instrument, each time interval for Doppler measurements having a minimum length determined by the required accuracy of the Doppler frequency estimation, the amplitude image being presented together with an indication of the region of Doppler measurement in real time on a display device, the region of Doppler measurement consisting of a small and localized region for pulsed wave overlap between transmitting and receiving transducer beams for continuous wave Doppler measurement, said apparatus comprising in combination, a Doppler measurement unit providing either pulsed or continuous wave mode measurement outputs, a pulse echo amplitude imaging unit, at least one ultrasonic transducer for the Doppler measurement and the amplitude imaging, said transducer being within communicable range of said Doppler measurement unit and said imaging unit and communicating therewith, a control unit for interlacing the Doppler measurement and amplitude imaging in time, with an associated display to present the imaging and/or spectral Doppler data in real time, said control unit being within communicable range of said Doppler measurement unit and said imaging unit and communicating therewith, and including means for interrupting said Doppler measurement repetitively to do at least significant fractions of complete sweeps of the ultrasonic beam over the amplitude image field to do a full update of the amplitude image for each interruption, means for generating a substitute signal with spectral content close to that of the Doppler measurement, said means being in communicating range of and communicating with said Doppler unit, said substitute signal being determined on the basis of the Doppler measurement, after being filtered through a Doppler instrument tissue filter, said substitute signal replacing said Doppler measurement at least when there is no useful Doppler measurement present, and an output device for presentation of the resulting synthesized Doppler signal, thereby providing an approximation of a simultaneous Doppler measurement, either pulsed or continuous wave, and amplitude imaging without any reduction in the maximum velocity measured solely by a freestanding Doppler instrument or without any reduction in the beam scanning rate for on amplitude image produced solely by a freestanding imaging instrument.

14. An apparatus according to claim 13, wherein said means for generating a substitute signal is for each estimation interval, adapted to form an estimate based upon a doppler signal curve during a certain time in association with said each estimation interval, said estimates replacing the Doppler measurement doppler signal during the estimation interval.

15. An apparatus according to claim 14, further comprising, a store for continuous storing of the Doppler measurement, and adapted to have the last stored part of the Doppler measurement read out, in order to form the estimate during each estimation interval.

16. An apparatus according to claim 15, further comprising means for determining a characteristic of the Doppler measurement, and a controlled filter, the instantaneous filter characteristic of which is adjusted on the basis of said Doppler measurement characteristic, for example the power spectrum thereof, and a source of broad-band noise connected to the filter so that the filter output delivers an estimate of the Doppler measurement.

17. An apparatus according to claim 16, further comprising means for introducing a window function in front of the tissue filter, said window function reducing the transient time of the tissue filter.

18. An apparatus according to claim 13, wherein said estimation is introduced into the path of said Doppler measurement after the tissue filter.

19. An apparatus according to claim 18, wherein the tissue filter characteristic is adapted to be changed from an increased frequency limit to a lower cut-off frequency during an interval of the same order of magnitude as the transient time of the tissue filter.

20. An apparatus according to claim 19, wherein a prefiltering network is incorporated in the tissue filter, said prefiltering network comprising a series capacitor filter, and a parallel resistor, wherein either the capacitor or the resistor or both are voltage controllable and adapted to be supplied with a control voltage for changing the filter characteristic.

21. An apparatus according to claim 13, further comprising means for adjusting or smoothing the Doppler measurement signal or the estimate signal at the transitions between doppler measurement and echo imaging, in particular at the termination of the estimate time.

22. An apparatus according to claim 21, wherein said smoothing means is adapted to multiply the signal or the signals by a suitable window function, for example a cosine function.

23. An apparatus according to claim 13, wherein said at least one ultrasonic transducer comprises a number of transducer elements located along a line, of which a portion of the transducer elements operates as transmitters in the doppler measurement, whereas the remaining portion of the transducer elements operates as receivers, and that the total number of transducer elements in the arrangement is adapted to operate during echo imaging.

24. An apparatus according to claim 13, wherein said output device provides for audible presentation of the resulting synthesized Doppler signal.

* * * * *